United States Patent
Grison et al.

(10) Patent No.: US 10,099,987 B2
(45) Date of Patent: Oct. 16, 2018

(54) PROCESS FOR PREPARING SYNTHESIS INTERMEDIATES USING PRODUCTS OF NATURAL ORIGIN AND USE OF THE INTERMEDIATES OBTAINED

(71) Applicants: CENTRE NATIONAL DE LA RECHERCHE SCIENTIFIQUE, Paris (FR); UNIVERSITE DE MONTPELLIER, Montpellier (FR)

(72) Inventors: Claude Grison, Castelnau-le-Lez (FR); Vincent Escande, Montpellier (FR); Andrii Stanovych, Jacou (FR)

(73) Assignees: CENTRE NATIONAL DE LA RECHERCHE SCIENTIFIQUE, Paris (FR); UNIVERSITE DE MONTPELLIER, Montpellier (FR)

( * ) Notice: Subject to any disclaimer, the term of this patent is extended or adjusted under 35 U.S.C. 154(b) by 0 days.

(21) Appl. No.: 15/536,612

(22) PCT Filed: Dec. 16, 2015

(86) PCT No.: PCT/FR2015/053559
§ 371 (c)(1),
(2) Date: Jun. 15, 2017

(87) PCT Pub. No.: WO2016/097612
PCT Pub. Date: Jun. 23, 2016

(65) Prior Publication Data
US 2017/0327449 A1    Nov. 16, 2017

(30) Foreign Application Priority Data
Dec. 16, 2014  (FR) ...................... 14 62548

(51) Int. Cl.
C07C 45/72    (2006.01)
C07C 45/75    (2006.01)

(52) U.S. Cl.
CPC .............. *C07C 45/75* (2013.01); *C07C 45/72* (2013.01)

(58) Field of Classification Search
CPC ................................ C07C 45/72; C07C 45/75
See application file for complete search history.

(56) References Cited

FOREIGN PATENT DOCUMENTS

GB    1465668 A    2/1977

OTHER PUBLICATIONS

Hermann Stetter, Catalyzed Addition of Aldehydes to Activated Double Bonds—A New Synthetic Approach, Angewandte Chemie, 1976, pp. 639-712, vol. 15, No. 11.
Niall W.A. Geraghty, et al., Synthesis of 2-Alkyl-2-cyclopenten-1-ones. A Versatile Kinetic Alkylation-Ozonolysis Procedure for the Preparation of γ-Ketoaldehydes, Synthesis, Aug. 1989, pp. 603-607.
Hermann Stetter, et al., Intramolekulare Aldol-Reaktion von δ,ε-Ungesättigten γ-Diketonen, Synthesis, Mar. 1979, pp. 187-188, Georg Thieme Publishers.
May 23, 2016, English Translation of International Search Report issued for related International Application No. PCT/FR2015/053559.

*Primary Examiner* — Sikarl A Witherspoon
(74) *Attorney, Agent, or Firm* — Young & Thompson

(57) ABSTRACT

Disclosed is a process for preparing a product of formula I: wherein the reaction is catalyzed both by thiamine or a thiamine salt and by ascorbic acid in a form which is free or salified or an organic acid salt of an alkaline metal, preferably sodium acetate, potassium tartrate, sodium succinate, or a reductone, preferably 2-hydroxypropanedial or 2,3-dihydroxycyclopent-2-ene-1-one in an organic solvent.

21 Claims, No Drawings

PROCESS FOR PREPARING SYNTHESIS INTERMEDIATES USING PRODUCTS OF NATURAL ORIGIN AND USE OF THE INTERMEDIATES OBTAINED

The synthetic chemistry industry is undergoing a paradigm shift. The current "all natural", "all organic" craze has created a new market oriented towards "green" products. Meanwhile, the toughening of the REACH regulation and the bad perception of chemistry among public opinion are converging towards a new approach to chemistry, which today aspires to be eco-friendly. This rapid evolution is reflected by the development of new environmentally friendly synthesis processes focused on the preparation of bio-sourced products. This is a real scientific and technical challenge, requiring innovation and integration of new synthesis strategies. The cosmetics industries are the first to be part of this process and are clearly demonstrating their interest in ecological and bio-inspired organic chemical processes. Here we describe a completely revamped Stetter reaction, based on the use of completely bio-sourced reagents and catalysts. This new green approach to the Stetter reaction allows a much more efficient access to derivatives that can be used in organic synthesis, and especially to 1,4-dicarbonyl derivatives (diketones and keto aldehydes) and to the corresponding cyclic ketones such as jasmonic derivatives. The originality of the methodology is based on the combined use of two vitamins: vitamin C and vitamin B1. The absence of a synthetic, corrosive, toxic base is helpful.

The methodology developed by Hermann Stetter in 1976 was described for example in the following publications: H. Stetter, *Angewandte Chemie International Edition in English* 1976, 15, 639-647; H. Stetter, H.-J. Bender, *Angewandte Chemie International Edition in English* 1978, 17, 131-131; H. Stetter, H. Kuhlmann, *Tetrahedron Letters* 1974, 15, 4505-4508; H. Stetter, H. Kuhlmann, W. Haese, *Organic Syntheses* 1987, 25, 26; and H. Stetter, H. Kuhlmann, *Organic Reactions* 1991, 40, 400.

This reaction allows especially the synthesis of 1,4-diketones in accordance with an "Umpolung" (reverse polarity) reaction. This reaction is directly inspired by the biological role of thiamine (vitamin B1), capable of temporarily transforming an aldehyde (electrophile) into a nucleophile. This reaction is usually conducted using a synthetic thiazolium derived from thiamine (3-benzyl-5-(2-hydroxyethyl)-4-methyl-1,3-thiazolium chloride), but with fewer functional groups than thiamine, these functional groups potentially being troublesome for the success of the reaction.

Moreover, this thiazolium must be deprotonated to attack the aldehyde, which explains the use of a base, typically triethylamine. This reaction is conducted in various solvents, primarily ethanol or dimethylformamide.

The present invention consists of developing a completely bio-sourced version of this reaction, which has thus led us to choose ethanol as solvent and to replace the Stetter thiazolium for real thiamine, which is a product of natural origin, although it is more difficult to react.

Since the aim of the present invention is to use, in the proposed syntheses, products having a base of natural origin, a large number of potential bases were tested, especially the following bases:

hydroxides obtained by hydration of the ashes or the action of soda on the ashes of Zn-accumulating plants described in application WO 2013/150197 (response tested under conventional heating and under microwave activation), hydroxides obtained by hydration of the ashes or the action of soda on the ashes of Zn-accumulating plants described in application WO 2011/064487 (response tested under conventional heating and under microwave activation), hydroxides obtained by hydration of the ashes or the action of soda on the ashes of Ni-accumulating plants described in application WO 2011/064487 (response tested under conventional heating and under microwave activation), citrates obtained by the action of citric acid on the ashes of Zn-accumulating plants described in application WO 2011/064487, acetates obtained by the action of acetic acid on the ashes of Zn-accumulating plants described in application WO 2011/064487, basic alumina, Na fluoride supported on alumina, fluorides obtained by the action of alkaline fluorides (Na, K) on the metal chlorides obtained by the action of hydrochloric acid on the ashes of Zn-accumulating plants described in application WO 2011/064487, supported on alumina.

urea
$CaCO_3$
$NaHCO_3$
arginine
copper-arginine complex
$Ca(OH)_2$
cysteine
asparagine
histidine
glycine
alanine
sodium glutamate
glutamine
arginine
threonine
lysine
serine
allantoin
riboflavin
chitosan
leucine
potassium gluconate
hydrated sodium acetate
hydrated sodium citrate
sodium salicylate
sodium oxalate
calcium oxalate
calcium citrate
pyrrolidine.

The tests that were carried out with these basic molecules of natural origin have led the inventors to exclude their use. This is particularly the case for the use of hydroxides, carbonates, hydrogen carbonates and amino acids (such as histidine or arginine, selected for their pKa), due to the total absence of reaction.

Some carboxylates showed a slight reactivity, which had actually been highlighted by Stetter for sodium acetate.

However, the yield was still modest with sodium acetate (55%) in cases in which the thiazolium used (natural thiamine) does not have the same reactivity as the molecule used by Stetter (3-benzyl-5-(2-hydroxyethyl)-4-methyl-1,3-thiazolium chloride). Other natural carboxylates proved to be relatively effective (sodium-potassium tartrate, sodium succinate), but without the overall efficiency exceeding 30%.

The inventors then turned to another natural molecule, sodium ascorbate.

This molecule, vitamin C, is usually used as a reducing agent in organic synthesis.

Its use as a basic reagent has never been described.

Its use in place of the triethylamine in the Stetter reaction, combined with vitamin B1 (thiamine), reaches 92% in the case of the reaction involving the substrates initially used by Stetter (heptanal and 3-buten-2-one), which exceeds the 75% described by this author.

This methodology differing from the original conditions is therefore a completely green alternative of natural origin, allowing access to carbonyl derivatives possessing an attractor group in position 4, such as 1,4-diketones, with excellent performance.

The present invention therefore relates to a process for preparing a product of formula I:

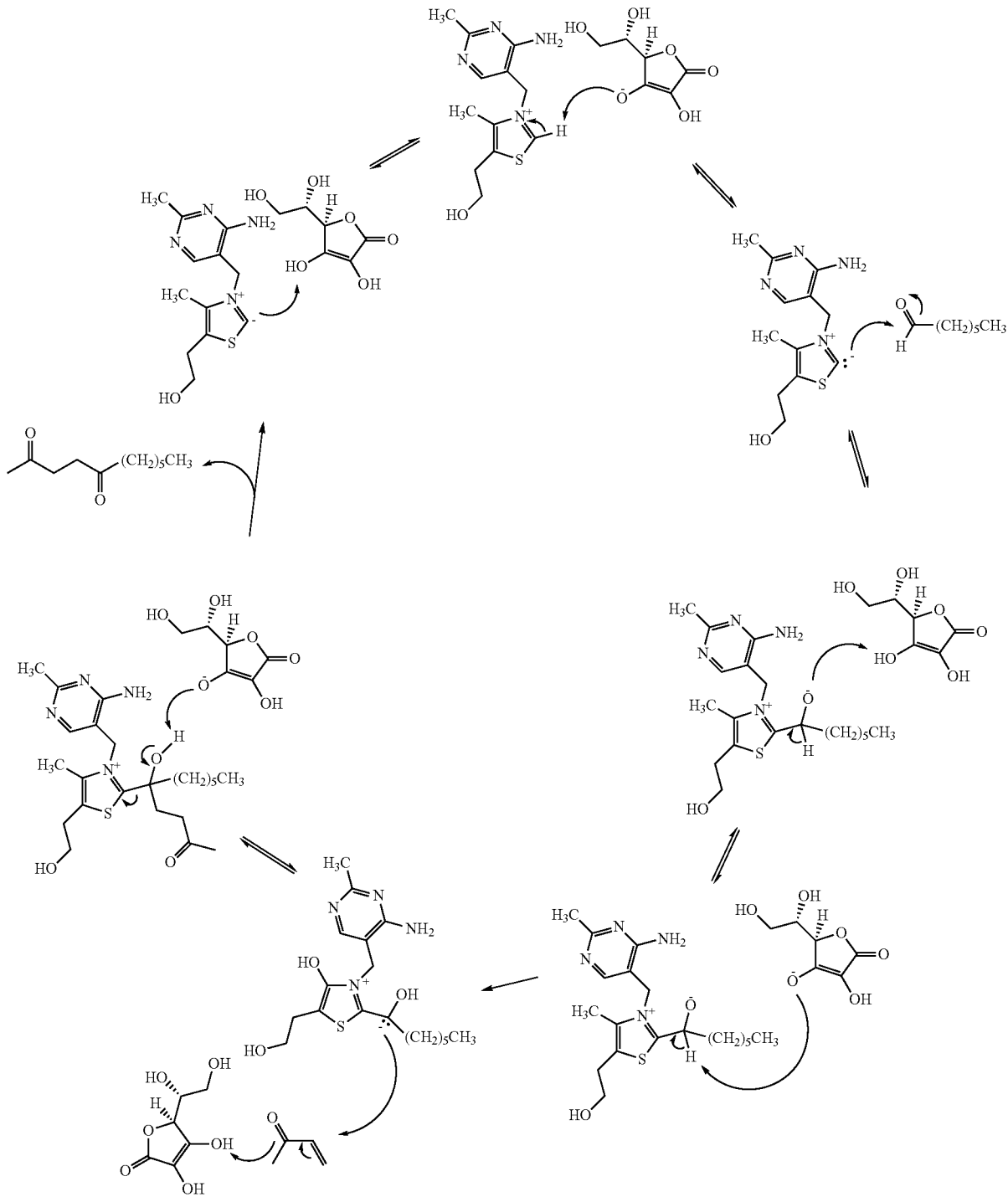

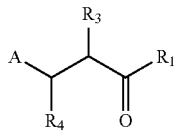

in which A represents a group selected from:

CO—$R_2$

CO—O—$R_2$a

CN

C(O)—N Ra R'a

CH—(CO$_2$Rb)$_2$ $R_1$ represents a hydrogen atom or a linear alkyl or branched alkyl or alkylene group having at most 12 carbon atoms, or $R_1$ represents a saturated or unsaturated cycloalkyl group having from 3 to 7 carbon atoms and optionally comprising one or more heteroatoms selected from the atoms of nitrogen, sulphur or oxygen, or $R_1$ represents a carbocyclic or heterocyclic aryl group, each of these alkyl, alkylene, aryl or cycloalkyl groups being optionally substituted, $R_2$ represents a linear or branched alkyl group having from 1 to 12 carbon atoms, optionally substituted, or $R_2$ represents a saturated or unsaturated cycloalkyl group having from 3 to 7 carbon atoms and optionally containing one or more heteroatoms selected from the atoms of nitrogen, sulphur or oxygen, or $R_2$ represents a carbocyclic or heterocyclic aryl group, each of these alkyl, aryl or cycloalkyl groups being optionally substituted, $R_2$a represents a linear or branched alkyl group having from 1 to 12 carbon atoms, Ra and R'a are identical or different and are selected from linear or branched alkyl or alkoxy groups having from 1 to 12 carbon atoms, it being understood that Ra and R'a cannot simultaneously represent each a linear or branched alkoxy group having from 1 to 12 carbon atoms, Rb is selected from linear or branched alkyl groups having from 1 to 12 carbon atoms $R_3$ represents a hydrogen atom, linear or branched alkyl or alkylene group having at most 6 carbon atoms, or $R_3$ represents a carbocyclic or heterocyclic aryl group, each of these alkyl, alkylene or aryl groups being optionally substituted, or the groups $R_2$ and $R_3$ are linked together to form a ring having from 5 to 7 carbon atoms, said chain optionally comprising one or more heteroatoms selected from the atoms of nitrogen, sulphur or oxygen, $R_4$ is a hydrogen atom or is selected from optionally substituted alkyl groups, or acylamido groups having from 2 to 12 carbon atoms, or carboxyl esters, with $R_4$ preferably representing a hydrogen atom, characterised in that a compound of formula II:

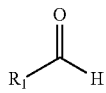

is reacted with a product of formula III:

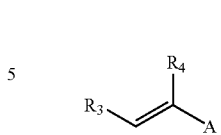

in the presence of both a thiazolium salt, a 1,3-imidazolium salt or a 1,2,4-triazolium salt, especially a thiazolium salt or a 1,2,4-triazolium salt, preferably a thiazolium salt, and ascorbic acid in a form which is free or a salt, or an organic acid salt of an alkaline metal, preferably sodium acetate, potassium tartrate or sodium succinate, or a compound comprising a structure

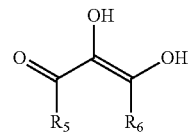

in which $R_5$ and $R_6$ independently of one another represent a hydrogen atom, a linear or branched alkyl group having from 1 to 12 carbon atoms, or $R_5$ and $R_6$ are linked together to form a ring having from 3 to 7 members, said alkyl or said ring being optionally substituted by one or more heteroatoms, especially selected from O, N and S, especially a reductone, preferably 2-hydroxypropanedial or 2,3-dihydroxycyclopent-2-en-1-one, or croconic acid, in an organic solvent.

Advantageously, the reaction is carried out with an unsaturated α,β-ketone, that is to say with a product of formula III:

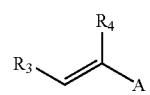

in which A represents a CO—$R_2$ group.

Advantageously, the reaction is carried out in the presence of both a thiazolium salt or a 1,2,4-triazolium salt, preferably a thiazolium salt, and ascorbic acid in a form which is free or a salt, or a compound comprising a structure

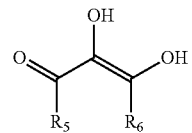

in which $R_5$ and $R_6$ independently of each other represent a hydrogen atom, a linear or branched alkyl group having from 1 to 12 carbon atoms, or $R_5$ and $R_6$ are linked together to form a ring having from 3 to 7 members, said alkyl or said ring being optionally substituted by one or more heteroatoms, especially selected from O, N and S, especially a reductone, preferably 2-hydroxypropanedial or 2,3-dihydroxycyclopent-2-en-1-one, or croconic acid, in an organic solvent.

The organic compound comprising at least one thiazolium ring is for example a compound of general formula A as follows:

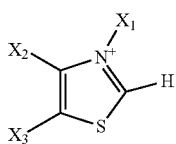

in which:

$X_1$ represents a $C_1$ to $C_6$ alkyl group, a $C_5$ to $C_{10}$ aryl group, especially phenyl, biphenyl or naphthyl, a $C_1$ to $C_6$ alkyl $C_5$ to $C_{10}$ aryl group, especially benzyl, a $C_5$ to $C_{10}$ heteroaryl group, especially pyridyl or pyrimidyl, said alkyl, alkylaryl and heteroaryl groups being able to be substituted by one or more heteroatoms, especially selected from N, O or S, $X_2$ represents hydrogen, a $C_1$ to $C_6$ alkyl group, especially methyl, ethyl or propyl, a $C_5$ to $C_{10}$ aryl group, especially phenyl, biphenyl or naphthyl, a $C_1$ to $C_6$ alkyl $C_5$ to $C_{10}$ aryl group, especially benzyl, a $C_5$ to $C_{10}$ heteroaryl group, especially pyridyl or pyrimidyl, said alkyl, aryl, alkylaryl and heteroaryl groups being able to be substituted by one or more heteroatoms, especially selected from N, O or S, $X_1$ represents a $C_1$ to $C_6$ alkyl group, a $C_5$ to $C_{10}$ aryl group, especially phenyl, biphenyl or naphthyl, a $C_1$ to $C_6$ alkyl $C_5$ to $C_{10}$ aryl group, especially benzyl, a $C_5$ to $C_{10}$ heteroaryl group, especially pyridyl or pyrimidyl, said alkyl, alkylaryl and heteroaryl groups being able to be substituted by one or more heteroatoms, especially selected from N, O or S.

The organic compound comprising at least one thiazolium ring advantageously has the following formula A1:

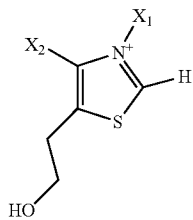

in which $X_1$ is as defined above, advantageously a heteroaryl or an alkylaryl, $X_2$ is advantageously as defined above, advantageously an alkyl.

The organic compound comprising at least one thiazolium ring is preferably thiamine or one of the salts thereof of the following formula:

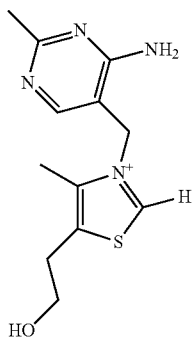 [SMILES: Cc1ncc(C[n+]2csc(CCO)c2C)c(N)n1]

The organic compound comprising at least one 1,2,4-triazolium ring is a compound of the following formula B:

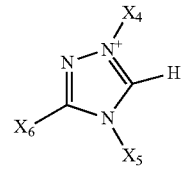

in which:

$X_4$ represents a $C_1$ to $C_6$ alkyl group, a $C_5$ to $C_{10}$ aryl group, especially phenyl, biphenyl or naphthyl, a $C_1$ to $C_6$ alkyl $C_5$ to $C_{10}$ aryl group, especially benzyl, a $C_5$ to $C_{10}$ heteroaryl group, especially pyridyl or pyrimidyl, said alkyl, aryl, alkylaryl and heteroaryl groups being able to be substituted by one or more heteroatoms, especially selected from N, O or S, $X_5$ represents hydrogen, a $C_1$ to $C_6$ alkyl group, especially methyl, ethyl or propyl, a $C_5$ to $C_{10}$ aryl group, especially phenyl, biphenyl or naphthyl, a $C_1$ to $C_6$ alkyl $C_5$ to $C_{10}$ aryl group, especially benzyl, a $C_5$ to $C_{10}$ heteroaryl group, especially pyridyl or pyrimidyl, said alkyl, aryl, alkylaryl and heteroaryl groups being able to be substituted by one or more heteroatoms, especially selected from N, O or S, $X_6$ represents a $C_1$ to $C_6$ alkyl group, a $C_5$ to $C_{10}$ aryl group, especially phenyl, biphenyl or naphthyl, a $C_1$ to $C_6$ alkyl $C_5$ to $C_{10}$ aryl group, especially benzyl, a $C_5$ to $C_{10}$ heteroaryl group, especially pyridyl or pyrimidyl, said alkyl, aryl, alkylaryl and heteroaryl groups being able to be substituted by one or more heteroatoms, especially selected from N, O or S, or $X_5$ and $X_6$ are linked together to form a ring having 5 or 6 members, especially 5 members, said ring being optionally substituted by an alkyl, aryl, heteroaryl or alkylaryl group. Said ring having 5 or 6 members substituted by an alkyl, aryl, heteroaryl or alkylaryl may be in the form of a mixture of enantiomers or may be a single enantiomer.

The present invention also relates to a process for preparing a product of formula I:

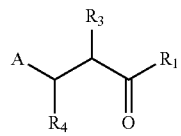

in which A represents a group selected from:
CO—$R_2$
CO—O—$R_2$a
CN
C(O)—N Ra R'a
CH—(CO$_2$Rb)$_2$ $R_1$ represents a hydrogen atom or a linear or branched alkyl or alkylene group having at most 12 carbon atoms, or $R_1$ represents a saturated or unsaturated cycloalkyl group having from 3 to 7 carbon atoms and optionally comprising one or more heteroatoms selected from the atoms of nitrogen, sulphur or oxygen, or $R_1$ represents a carbocyclic aryl group or heterocyclic aryl group, each of these alkyl, alkylene, aryl or cycloalkyl groups being optionally substituted, $R_2$ represents a linear or branched alkyl group having from 1 to 12 carbon atoms, optionally substituted, or $R_2$ represents a saturated or unsaturated cycloalkyl group having from 3 to 7 carbon atoms and optionally comprising one or more heteroatoms selected from the atoms of nitrogen, sulphur or oxygen, or $R_2$ represents a carbocyclic or heterocyclic aryl group, each of these alkyl, aryl or cycloalkyl groups being optionally substituted, $R_2a$ represents a linear or branched alkyl group having from 1 to 12 carbon atoms, Ra and R'a, identical or different, are chosen from linear or branched alkyl or alkoxy groups having from 1 to 12 carbon atoms, it being understood that Ra and R'a cannot simultaneously represent each a linear or branched alkoxy group having from 1 to 12 carbon atoms, Rb is selected from linear or branched alkyl groups having from 1 to 12 carbon atoms, $R_3$ represents a hydrogen atom, a linear or branched alkyl or alkylene group having at most 6 carbon atoms, or $R_3$ represents a carbocyclic or heterocyclic aryl group, each of these alkyl, alkylene or aryl groups being optionally substituted, or the groups $R_2$ and $R_3$ are linked together to form a ring having from 5 to 7 carbon atoms, said chain optionally comprising one or more heteroatoms selected from the atoms of nitrogen, sulphur or oxygen, $R_4$ is a hydrogen atom or is selected from optionally substituted alkyl groups, acylamido groups having from 2 to 12 carbon atoms, or carboxyl esters, with $R_4$ preferably representing a hydrogen atom, characterised in that a product of formula II:

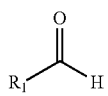

II is reacted with a product of formula III:

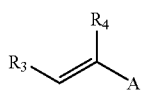

III in the presence of both thiamine or a thiamine salt and ascorbic acid in a form which is free or a salt, or an organic acid salt of an alkaline metal, preferably sodium acetate, potassium tartrate or sodium succinate, or a compound comprising a structure

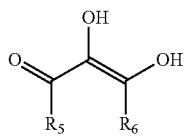

in which $R_5$ and $R_6$ independently of one another represent a hydrogen atom, a linear or branched alkyl group having from 1 to 12 carbon atoms, or $R_5$ and $R_6$ are linked together to form a ring having from 3 to 7 members, said alkyl or said ring being optionally substituted by one or more heteroatoms, especially selected from O, N and S, especially a reductone, preferably 2-hydroxypropanedial or 2,3-dihydroxycyclopent-2-en-1-one or croconic acid, in an organic solvent.

In the foregoing, the reaction is carried out, during the reaction between products II and III, in simultaneous presence of thiamine or a thiamine salt and one (or several) of the products selected from ascorbic acid in a form which is free or a salt or a compound comprising a structure

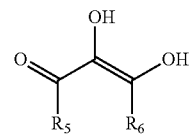

in which $R_5$ and $R_6$ independently of one another represent a hydrogen atom, a linear or branched alkyl group having from 1 to 12 carbon atoms, or $R_5$ and $R_6$ are linked together to form a ring having from 3 to 7 members, said alkyl or said ring being optionally substituted by one or more heteroatoms, especially selected from O, N and S, especially a reductone, preferably 2-hydroxypropanedial or 2,3-dihydroxycyclopent-2-en-1-one or croconic acid.

The present invention also relates to a process for preparing a product of formula I:

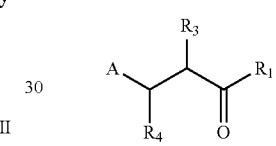

I in which A represents a group selected from:
CO—$R_2$
CO—O—$R_2a$
CN
C(O)—N Ra R'a
CH—$(CO_2Rb)_2$ $R_1$ represents a hydrogen atom or a linear or branched alkyl or alkylene having at most 12 carbon atoms, or $R_1$ represents a saturated or unsaturated cycloalkyl group having from 3 to 7 carbon atoms and optionally comprising one or more heteroatoms selected from the atoms of nitrogen, sulphur or oxygen, or $R_1$ represents a carbocyclic or heterocyclic aryl group, each of these alkyl, alkylene, aryl or cycloalkyl groups being optionally substituted, $R_2$ represents a linear or branched alkyl group having from 1 to 12 carbon atoms, optionally substituted, or $R_2$ represents a saturated or unsaturated cycloalkyl group having from 3 to 7 carbon atoms and optionally comprising one or more heteroatoms selected from the atoms of nitrogen, sulphur or oxygen, or $R_2$ represents a carbocyclic or heterocyclic aryl group, each of these alkyl, aryl or cycloalkyl groups being optionally substituted, $R_2a$ represents a linear or branched alkyl group having from 1 to 12 carbon atoms, Ra and R'a, identical or different, are selected from linear or branched alkyl or alkoxy groups having from 1 to 12 carbon atoms, it being understood that Ra and R'a cannot simultaneously represent each a linear or branched alkoxy group having from 1 to 12 carbon atoms, Rb is selected from linear or branched alkyl groups having from 1 to 12 carbon atoms, $R_3$ represents a hydrogen atom, linear or branched alkyl or alkylene group having at most 6 carbon atoms, or $R_3$ represents a carbocyclic or heterocyclic aryl group, each of these alkyl, alkylene or aryl groups being optionally substituted, $R_4$ is a hydrogen atom or is selected from optionally substituted alkyl groups, acylamido groups having from 2 to 12 carbon atoms, or carboxyl esters, with $R_4$ preferably representing a hydrogen atom, characterised in that a product of formula II:

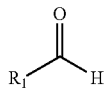

II is reacted with a product of formula III:

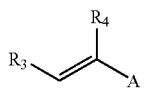

III in the presence of both thiamine or a thiamine salt and ascorbic acid in a form which is free or a salt, or an organic acid salt of an alkaline metal, preferably sodium acetate, potassium tartrate or sodium succinate, or a compound comprising a structure

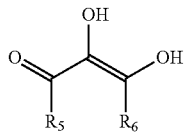

in which $R_5$ and $R_6$ independently of one another represent a hydrogen atom, a linear or branched alkyl group having from 1 to 12 carbon atoms, or $R_5$ and $R_6$ are linked together to form a ring having from 3 to 7 members, said alkyl or said ring being optionally substituted by one or more heteroatoms, especially selected from O, N and S, especially a reductone, preferably 2-hydroxypropanedial or 2,3-dihydroxycyclopent-2-en-1-one or croconic acid, in an organic solvent.

In the foregoing, the reaction is carried out, during the reaction between products II and III, in simultaneous presence of thiamine or a thiamine salt and one (or several) of the products selected from ascorbic acid in a form which is free or a salt, or an organic acid salt of an alkaline metal, preferably sodium acetate, potassium tartrate or sodium succinate, or a compound comprising the structure

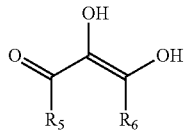

in which $R_5$ and $R_6$ independently of one another represent a hydrogen atom, a linear or branched alkyl group having from 1 to 12 carbon atoms, or $R_5$ and $R_6$ are linked together to form a ring having from 3 to 7 members, said alkyl or said ring being optionally substituted by one or more heteroatoms, especially selected from O, N and S, especially a reductone, preferably 2-hydroxypropanedial or 2,3-dihydroxycyclopent-2-en-1-one or croconic acid.

Preferably, the reaction is carried out, during the reaction between products II and III, in simultaneous presence of thiamine or a thiamine salt and one (or several) of the products selected from ascorbic acid in a form which is free or a salt, or a compound comprising a structure

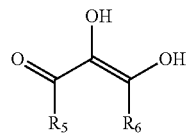

in which $R_5$ and $R_6$ independently of one another represent a hydrogen atom, a linear or branched alkyl group having from 1 to 12 carbon atoms, or $R_5$ and $R_6$ are linked together to form a ring having from 3 to 7 members, said alkyl or said ring being optionally substituted by one or more heteroatoms, especially selected from O, N and S, especially a reductone, preferably 2-hydroxypropanedial or 2,3-dihydroxycyclopent-2-en-1-one or croconic acid.

The aldehyde reagent $R_1CHO$ can be an aliphatic, aromatic, carbocyclic or heterocyclic aldehyde, but also formaldehyde ($R_1$=H), which does not lead to the product I in the case of the conventional Stetter reaction.

The alkyl groups that can be represented by $R_1$, $R_2$, $R_3$ et $R_4$ preferably can be functionalised by another structure, for example a carbonyl group (ketone or aldehyde) in a form which is free or protected in the form of a ketal, or a carboxy in free form or in the form of a carboxylic ester, or can be substituted by a heterocyclic aryl.

As indicated above, the preferred reductones are 2-hydroxypropanedial or 2,3-dihydroxycyclopent-2-en-1-one. These products also have other names, for example, respectively, tartronaldehyde or hydroxypropanedial and reductic acid.

Their developed formulas are indicated below:

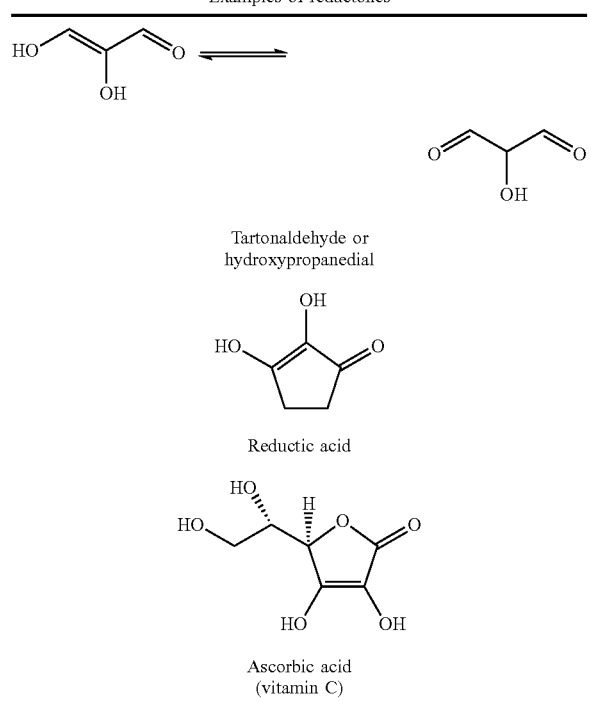

For its part, croconic acid has the following formula:

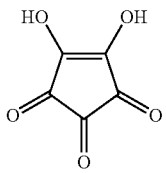

Especially, the invention relates to a process as described above, characterised in that the substituent(s) which can be carried by the linear or branched alkyl or alkylene groups, the carbocyclic or heterocyclic aryl groups, or cycloalkyl groups are selected from the carbocyclic or heterocyclic aryl groups, themselves optionally substituted, the esterified or a salt free carboxylic groups, the free oxo group in the form of a ketone or protected in the form of a ketal, the halogen atoms, or the alkoxy groups having from 1 to 6 carbon atoms, such as methoxy or ethoxy.

$R_1$ and $R_2$ may represent an alkyl or alkenyl group preferably having at most 9 carbon atoms and even more preferably at most 7 carbon atoms.

The alkyl groups are preferably substituted by a free oxo group in the form of a ketone or protected in the form of a ketal.

The carbocyclic aryl groups are chosen preferably from the phenyl groups optionally mono-substituted, di-substituted or tri-substituted by one or more groups selected from the alkyl or alkoxy groups having from 1 to 6 carbon atoms, a hydroxy group, a halogen atom, a cyano group, trifluoromethyl, alkylenedioxy having from 1 to 6 carbon atoms, or the naphthyl group.

The heterocyclic, monocyclic or condensed aryl groups are preferably selected from pyridyl, quinolinyl, isoquinolinyl, benzothienyl, benzofuranyl, benzopyranyl, benzothiopyranyl, furanyl, pyrrolyl, thiazolyl, oxazolyl, isoxazolyl, triazolyl, tetrazolyl, pyrazolyl, imidazolyl, thienyl, or phthalimide groups or from any one of said groups substituted by an alkyl or an alkoxy having from 1 to 12 carbon atoms, or a halogen.

The saturated or unsaturated mono- or bicyclic cycloalkyl groups having 3 to 7 carbon atoms and optionally comprising one or more heteroatoms selected from the atoms of nitrogen, sulphur or oxygen are preferably selected from the cyclopropyl, cyclobutyl, cyclopentyl, cyclohexyl, cycloheptyl, cyclooctyl, cyclopropenyl, cyclobutenyl, cyclopentenyl, cyclohexenyl, cycloheptenyl, 1,3-cyclohexadienyl, 1,4-cyclohexadienyl, 1,5-cyclohexadienyl, and bicycloheptenyl groups.

The group of mono- or bicyclic heterocycloalkyls, that is to say the cycloalkyls comprising one or more heteroatoms selected from the atoms of nitrogen, sulphur or oxygen, may include the following groups: aziridinyl, pyrrolidinyl, pyrrolidino, piperidinyl, piperazinyl, piperazino, morpholinyl, thiomorpholinyl, tetrahydrofuranyl, tetrahydrothiofuranyl, tetrahydropyranyl, dihydropyranyl, dioxanyl, dioxolanyl and pyranyl.

The carboxyl group may be esterified by an alkyl group having 1 to 4 carbon atoms, such as a methyl, ethyl or tert-butyl group, and the alkyl group may be substituted by one or more halogen atoms such as fluorine, chlorine or bromine, such as trifluoromethyl.

The halogen atoms are selected from the atoms of fluorine, chlorine bromine or iodine.

The alkoxy groups have from 1 to 12 carbon atoms and preferably from 1 to 7 carbon atoms. The preferred groups are methoxy, ethoxy, propyloxy, isopropyloxy, n-butoxy or tert-butyloxy, $R_1$, $R_2$ and $R_3$ may also represent one of the aforementioned carbocyclic or heterocyclic aryl groups, optionally substituted;

The values of $R_1$, $R_2$, $R_3$ and $R_4$ chosen from the values indicated above may be the same or different.

Preferably, $R_1$ is selected from a hydrogen atom or a linear or branched alkyl group having from 1 to 9 carbon atoms, preferably methyl, ethyl, n-propyl, butyl, isobutyl, tert-butyl, hexyl, octyl, nonyl or a linear or branched alkylene group having at most 9 carbon atoms, preferably 1-pentenyl, 1-hexenyl, 2,6-dimethyl-5-heptenyl, 2,6-dimethyl-1,5 dienyl heptyl, 1-nonenyl, a benzyl or a phenyl group, an aromatic or non-aromatic heterocycle containing oxygen or nitrogen, and more preferably n-propyl, butyl, isobutyl, or tert butyl hexyl, octyl, nonyl or a linear or branched alkylene group having at most 9 carbon atoms, preferably 1-pentenyl, 1-hexenyl, 3-hexenyl, 2,6-dimethyl-5-heptenyl, 2,6-dimethyl-1,5 dienyl heptyl, 1-nonenyl, a benzyl or a phenyl group, these groups being able to be substituted as indicated above.

The substituents $R_2$ and $R_2a$ may represent preferably a linear or branched alkyl group having from 1 to 9 carbon atoms, preferably methyl, ethyl, n-propyl, butyl, isobutyl, tert-butyl, hexyl, octyl and nonyl.

The substituents Ra and R'a may represent the same values as those mentioned above when they represent a linear or branched alkyl group having from 1 to 9 carbon atoms, preferably n-propyl, isobutyl, hexyl, octyl, nonyl or a linear or branched alkylene group having at most 9 carbon atoms, preferably 1-pentenyl, 1-hexenyl, 2,6-dimethyl-5-heptenyl, 2,6-dimethyl-1,5 dienyl heptyl, 1-nonenyl; Ra and R'a may also represent a benzyl group or a phenyl group.

Ra and R'a can also represent the corresponding alkoxy values, such as methoxy or ethoxy, for example.

Rb is selected from the aforementioned alkyl values and preferably has from 1 to 7 carbon atoms.

$R_3$ may represent one of the previously cited alkyl or aryl values. Preferably, $R_3$ represents a hydrogen atom or an alkyl group, preferably a methyl group, substituted by a free oxo group in the form of a ketone or protected in the form of a ketal, a diol protected in the form of a ketal, or a carboxylic group in a form which is free, a salt or esterified for example by an alkyl group having from 1 to 4 carbon atoms or by a carbocyclic or heterocyclic aryl group. Even more preferably, $R_3$ represents a hydrogen atom.

The acylamido value that can be represented by $R_4$ is preferably the acetylamido value.

$R_4$ may also represent preferably a hydrogen atom, an alkyl group, preferably a methyl group substituted by a free oxo group in the form of a ketone or protected in the form of a ketal, or a carboxyl group in a form which is free, a salt or esterified, for example by an alkyl group having from 1 to 4 carbon atoms.

When the groups $R_2$ and $R_3$ are linked together to form a ring having 5 to 7 carbon atoms, said ring is preferably a cyclopentenone.

The present invention especially relates to a process relating to the process described above for preparing a product of formula Ia

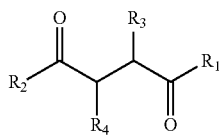

in which $R_1$, $R_3$ et $R_4$ have the meaning indicated above and corresponding to a product of formula I as defined above, in which A represents a CO—$R_2$ group, in which $R_2$ has the meaning indicated above, characterised in that a product of formula II as defined above is reacted with a product of formula IIIa:

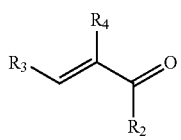

in the presence of thiamine or a thiamine salt, preferably thiamine hydrochloride and ascorbic acid in a form which is free or a salt, preferably sodium ascorbate, in an organic solvent, preferably ethanol.

The reaction is conducted at a temperature of from 50 to 120° C., preferably from 70 to 90° C.

The solvent in which the reaction is carried out is advantageously an alcohol, especially selected from methanol, ethanol, 1-propanol, 2-propanol, butanol, a polyol, particularly a diol such as 1,2-propanediol or 1,3-propanediol, or a triol such as glycerol. The solvent may also be a mixture of these alcohols or polyols, a mixture of an alcohol or a polyol with an organic solvent, or a mixture of an alcohol or a polyol and water. It is preferably ethanol, 1-propanol, 2-propanol, 1,2-propanediol, 1,3-propanediol, glycerol and water or a mixture of two or more of these solvents. Preferably, the solvent is a diol or a triol, especially 1,2-propanediol, 1,3-propanediol, glycerol or a mixture of two or three of these solvents.

The reaction is conducted preferably under dinitrogen current, during a period of 30 minutes to 30 hours, particularly about 1 to 12 hours, preferably about 2 hours.

The amount of solvent is advantageously from 1 to 5 L, especially about 2.5 liters of solvent per mole of product IIIa. About 1 to 5 liters of ethanol per mole of product IIIa are preferably used.

An excess of product of formula II relative to the product of formula III or IIIa is preferably used. This excess may be of the order of from 4/1 to 1.1/1, particularly 2/1, for example between 1.5 and 2.5, preferably 2. About 0.1 mole of thiamine or a thiamine salt is used for 1 mole of product of formula II, and 0.2 to 1.4 moles, particularly 0.2 to 0.8, preferably about 0.6 mole of ascorbic acid in a form which is free or a salt is used for 1 mole of product of formula II. The ratio of thiamine/ascorbic acid in a form which is free or a salt ranges from ½ to 1/20, preferably from ½ to 1/10, more advantageously from 1/3 to 1/7, and is preferably 1/5 or 1/6.

The process can be carried out by mixing the ascorbic acid in a form which is free or a salt and the thiamine salt and then adding to this mixture the product of formula II and the product of formula III or IIIa. Advantageously, the ascorbic acid in a form which is free or a salt and the thiamine salt are stirred in the solvent for a period of 1 to 30 minutes, especially about 10 minutes, before the addition of the products of formula II and III or IIIa.

The process can also be carried out by adding the mixture of ascorbic acid in a form which is free or a salt and thiamine salt to the mixture of products of formula II and III or IIIa. In one advantageous embodiment, the mixture of ascorbic acid in a form which is free or a salt and thiamine salt is added in portions. In another advantageous embodiment, the thiamine salt is added in portions to a mixture of products of formula II and III or IIIa and ascorbic acid in a form which is free or a salt.

The term "added in portions" in the sense of the present invention means that the total amount of ascorbic acid in a form which is free or a salt and thiamine salt is added several times during the reaction. According to an advantageous embodiment, the ascorbic acid in a form which is free or a salt and thiamine salt are added in portions of 25% then 25%, then 25%, then 25% of the total amount of ascorbic acid in a form which is free or a salt and thiamine salt.

In another preferred embodiment, the thiamine salt is added in four portions each of 25% to the mixture of products of formula II and III or IIIa and ascorbic acid in a form which is free or a salt.

The following reaction scheme illustrates the process of the invention:

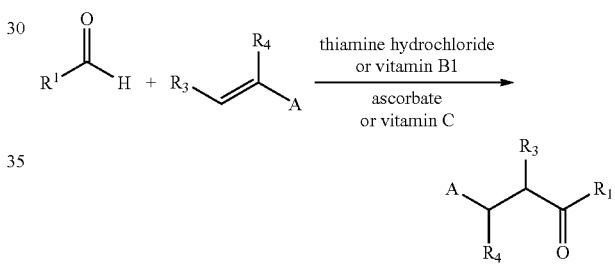

The Michael acceptor:

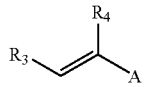

can be a ketone (A=—CO—$R_2$), an ester, (A=—CO—O—$R_2$a), or an α,β ethylenic nitrile (A=—CN).

It can carry other functional groups, such as a ketal, a carboxy ester, or a bicycloheptenyl.

The inventors have also shown that, under the reaction conditions described above, in the presence of both a thiazolium salt, a 1,3-imidazolium salt or a 1,2,4-triazolium salt as defined above and ascorbic acid which is in free or a salt form, or a compound comprising a structure

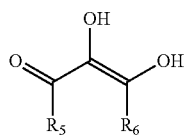

in which $R_5$ and $R_6$ independently of each other represent a hydrogen atom, a linear or branched alkyl group having from 1 to 12 carbon atoms or $R_5$ and $R_6$ are linked together to form a ring having from 3 to 7 members, said alkyl or said ring being optionally substituted by one or more heteroatoms, especially chosen from O, N and S, especially a reductone, preferably 2-hydroxypropanedial or 2,3-dihydroxycyclopent-2-en-1-one or croconic acid in an organic solvent, but in the absence of a compound of formula III or IIIa, self condensation of the aldehyde was observed (acyloin condensation).

The present invention therefore also relates to a process for preparing a compound of formula III':

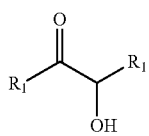

characterised in that a product of formula II:

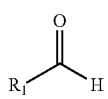

in which:

$R_1$ represents an alkyl group or linear or branched alkylene having at most 12 carbon atoms, or $R_1$ represents a saturated or unsaturated cycloalkyl group having from 3 to 7 carbon atoms and optionally comprising one or more heteroatoms selected from the atoms of nitrogen, sulphur or oxygen, or $R_1$ represents a carbocyclic or heterocyclic aryl group, each of these alkyl, alkylene, aryl or cycloalkyl groups being optionally substituted, is reacted in the presence of both a thiazolium salt, a 1,3-imidazolium salt, or a 1,2,4-triazolium salt, as defined above, and ascorbic acid in a form which is free or a salt, or a compound comprising a structure

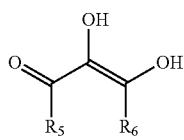

in which $R_5$ and $R_6$ independently of each other represent a hydrogen atom, a linear or branched alkyl group having from 1 to 12 carbon atoms, or $R_5$ and $R_6$ are linked together to form a ring having from 3 to 7 members, said alkyl or said ring being optionally substituted by one or more heteroatoms, especially selected from O, N and S, especially a reductone, preferably 2-hydroxypropanedial or 2,3-dihydroxycyclopent-2-en-1-one, or croconic acid, in an organic solvent, but in the absence of a compound of formula III or IIIa.

Preferably, when the group $R_1$ is alkylene or an unsaturated cycloalkyl group, the one or more double bonds is/are not conjugated to the aldehyde function.

Preferably, the reaction is carried out under the conditions described above, and particularly preferably in the presence of vitamin B1 and ascorbic acid in a form which is free or a salt.

Among the various Michael adducts derived from the Stetter reaction, it is known that 1,4-dicarbonyl derivatives are the direct precursors of many 5-membered heterocycles. They especially are of particular interest in the field of cosmetic derivatives. They are natural precursors of cyclopentenones, and therefore jasmonic derivatives.

For example, using the catalysts described in the application PCT/FR2014/052280 of 12 Sep. 2014 published as WO 2015/036714, the inventors have shown that it is possible to prepare dihydrojasmone using bio-sourced basic catalysts:

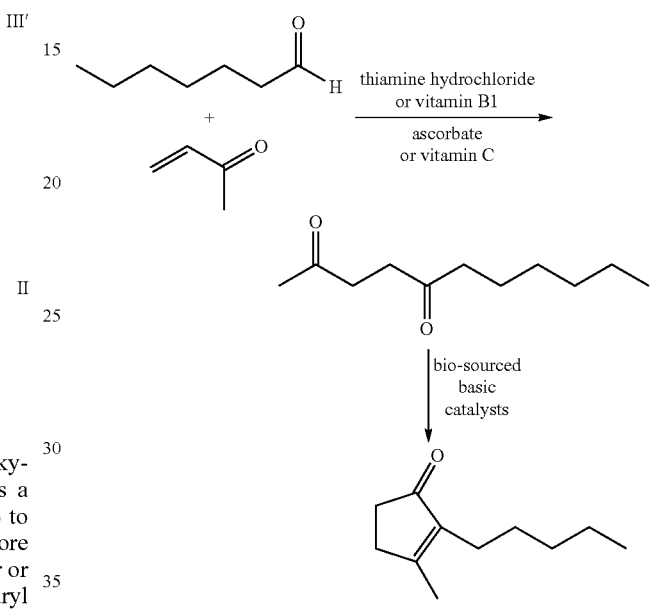

The present invention thus also relates to a process for preparing a product of formula IV':

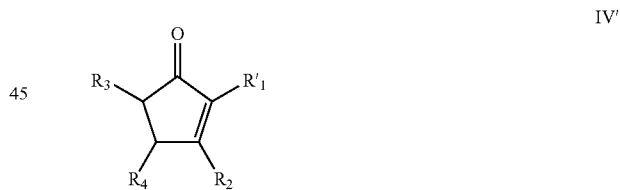

in which $R'_1$ represents a hydrogen atom or an alkyl group having at most 11 carbon atoms, which are optionally substituted, $R_2$ and $R_3$ having the meaning indicated above, it being understood that if $R_3$ and $R_4$ each represent a hydrogen atom and $R'_1$ represents a pentyl group, then $R_2$ cannot represent a methyl group, characterised in that a product of formula I'a:

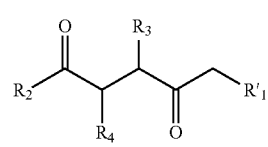

is reacted with a metal catalyst, preferably a catalyst obtained from materials of organic origin containing alkaline or alkaline earth metals, preferably calcium.

The cyclisation reaction leading to a pentenone ring can also be performed in the case where $R_2$ represents a hydrogen atom.

The present invention therefore also relates to a process for preparing a product of formula IV":

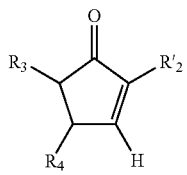

in which $R'_2$ represents a hydrogen atom or an alkyl group having at most 11 carbon atoms, optionally substituted, and $R_2$ and $R_3$ have the meaning indicated above,
characterised in that a product of formula I"a

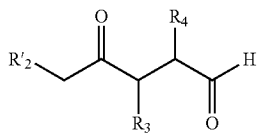

is reacted with a metal catalyst, preferably a catalyst obtained from materials of organic origin containing alkaline or alkaline earth metals, preferably calcium.

The groups $R'_1$ and $R'_2$ can carry the same substituents as the groups $R_1$ and $R_2$.

The materials of organic origin containing alkaline or alkaline earth metals, preferably calcium, and usable as basic catalyst used in the cyclisation reactions indicated above are preferably formed from an extract of a plant or part of a plant, from an alga or part of an alga having a high level of calcium (Ca) in an amount preferably greater than 50,000 ppm by weight, and containing less than 5,000 ppm of metals selected from zinc (Zn), nickel (Ni), manganese (Mn), lead (Pb), cadmium (Cd), copper (Cu), palladium (Pd) or marine shells or non-marine mollusc shells containing a high level of alkaline or alkaline earth metal, preferably calcium (Ca), preferably in the form of calcium carbonate, in an amount of preferably greater than 80%, more preferably greater than 90% by weight, optionally after drying and/or grinding and heat and/or chemical treatment, said catalyst being in the form of calcium oxide, calcium salt selected from oxalate, carbonate, phosphates such as phytate, simple carboxylates such as citrate, or sodium carboxylates such as alginate-type uronates or polygalacturonates or calcium hydroxide.

The plant comprising a high level of calcium (Ca) in an amount preferably greater than 50,000 ppm by weight, in the form of salt such as calcium oxalate or calcium carbonate is preferably a plant selected from:
the chenopodiaceae, preferably lamb's quarter
the plantaginaceae, preferably greater plantain
the portulacaceae, preferably common purslane
calcifying algae, preferably lithothamnium.

The catalysts can be prepared as follows:
CAT A1: 420 g of dehydrated samples of plants rich in Ca, preferably plantain, are burned in a muffle furnace at 500° C. for 7 h. 183 g of a solid rich in metal carbonates are obtained.
supported CAT A1: 1.7 g of a solid rich in metal carbonates are co-ground with 5 g of support (e.g. basic alumina, montmorillonite) and then activated by heating for 15 minutes at 150° C.
The solid rich in carbonate also comprises other anions, such as phosphates.
CAT A2: 10 g of metal carbonates produced from the previous heat treatment are introduced into a beaker and mixed with water while stirring. 30 mL of water are added. A grey suspension is obtained; stirring is continued for 1 h.
After decantation, the pH is 10. The mixture is concentrated on a rotary evaporator and dried in an oven at 80° C. 10.1 g of a grey powder are obtained.
supported CAT A2: 1.7 g of metal carbonates are co-ground with 5 g of support (e.g. basic alumina), and then activated by 15 minutes of heating at 150° C.
CAT A3: 10 g of CAT A1 are introduced into a 250 ml flask with 50 ml of HCl 12M added under stirring. The solution obtained is filtered through celite. After evaporation and concentration, 4.9 g of a solid is collected and dried at 80° C. 3 g of the above solid are dissolved in 70 mL of distilled water with a few drops of HCl to promote complete dissolution. The precipitation of metal hydroxides is performed by adding a concentrated sodium solution to pH=13. A white suspension is obtained. It is centrifuged. 2.7 g of solid are obtained and stored in an oven.
CAT A5: the catalyst derived from oyster shells is prepared as follows:
The shells are placed directly into a calciner. This is heated to 1000° C. for about 7 h. The resulting powder, which is very rich in calcium oxide, is kept under inert atmosphere, or used directly. In this case, it is rehydrated by incremental additions in water. The pH is then about 12. The resulting aqueous phase may be the reaction medium or may undergo a sequence of filtration/oven drying. In this case, the solid obtained can be used as a catalyst or reagent in another medium, such as an ethanolic medium.

The working conditions in which the cyclisation reaction is carried out may be described as follows:
0.5 M product of formula I'a or I"a is diluted in a mixture of water and ethanol (80/20 mL). 500 mg of plantain hydroxides prepared by alkaline hydrolysis of the corresponding chlorides (CAT A3) or from CAT A5. The solution was refluxed for 16 h, then extracted with ether. Monitoring of the reaction by GC MS shows complete formation of the dihydrojasmone. The catalyst was recycled by filtration, washing with water, with ethanol and then with acetone and drying for 4 h at 120° C.

The inventors of the present application have also found that, in an entirely unexpected manner, if the aldehyde substrate is conjugated to an ethylenic double bond (for example: 2-heptenal), the vitamin C/vitamin B1 cocktail can lead either to the unsaturated diketone as described above, or directly to the corresponding cyclopentenone without the addition of an additional base or of a basic catalyst being necessary, contrary to the Stetter conditions, leading to a cyclisation of the 1,4-dicarbonyl compound after addition of a base such as NaOH.

Generally, when the aldehyde substrate is conjugated to an ethylenic double bond, cyclisation leading to the cyclopentenone is produced spontaneously at least partly under the conditions of the Stetter reaction as modified by the inventors of the present invention (cocktail of vitamin C/vitamin B1 preferred).

It was further unexpectedly found that the percentage of cyclisation increases when excess vitamin C (ascorbic acid salt or ascorbic acid) is introduced into the reaction medium.

In the case of this process, by adjusting the reaction conditions as indicated above, the cyclisation may be spontaneous on all or substantially all of the intermediate unsaturated 1,4-dicarbonyl, formed from an enal.

The present invention therefore also relates to the preparation of a product of formula IVi:

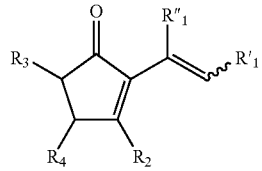

IVi in which $R'_1$ represents a linear or branched alkyl or alkylene group having at most 12 carbon atoms, optionally substituted, or $R'_1$ represents a carbocyclic or heterocyclic aryl group, $R''_1$ represents a hydrogen atom or an alkyl group having at most 6 carbon atoms, characterised in that a product of formula IIi

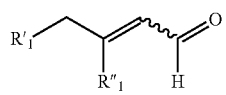

IIi is reacted with a product of formula IIIa:

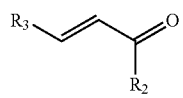

IIIa as defined above in the presence of thiamine or a thiamine salt, preferably thiamine hydrochloride and ascorbic acid in a form which is free or a salt, preferably sodium ascorbate, in an organic solvent to obtain a product of formula Ii:

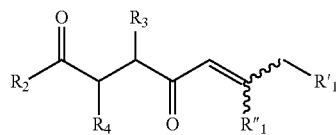

Ii which is a product of formula Ii which is spontaneously converted into a product of formula IVi in the presence of thiamine or a thiamine salt, preferably thiamine hydrochloride, and ascorbic acid in a form which is free or a salt, preferably sodium ascorbate, preferably in the presence of an excess of sodium ascorbate.

Without this constituting a limitation to the present invention, the inventors believe that the effect leading to spontaneous cyclisation of the product of formula I'b is due solely to the action of vitamin C added initially. The totally unexpected action thereof could be demonstrated by preparation of the unsaturated 1,4-dicarbonyl intermediate according to standard Stetter conditions (sole product with $Et_3N$ as the base), and then reacting this intermediate with vitamin C: cyclisation occurs up to a 31% yield:

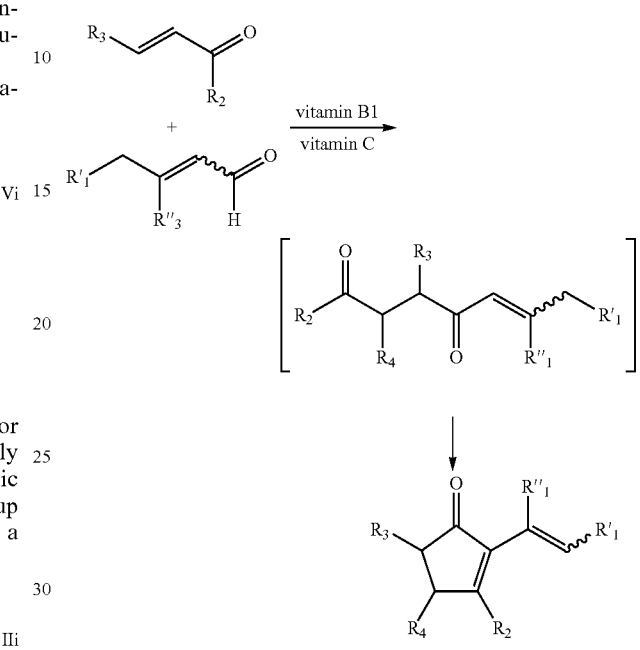

The present invention also relates to the use of a mixture of a thiazolium salt, a 1,3-imidazolium salt or a 1,2,4-triazolium salt, especially a thiazolium salt or a 1,2,4-triazolium salt, preferably a thiazolium salt, and ascorbic acid in a form which is free or a salt for the preparation of linear 1,4-dicarbonyl compounds, preferably the products of formulas I, Ia, I'a, I''a or Ii or cyclopentenones, such as dihydrojasmone and derivatives thereof, preferably the products of formulas IV', IV''' or IVi, preferably in a reaction of the Stetter type.

The present invention further relates to the use of a mixture of vitamin B1 (thiamine) or of a thiamine salt and ascorbic acid in a form which is free or a salt for the preparation of linear 1,4-dicarbonyl compounds, preferably the products of formulas I, Ia, I'a, I''a or Ii or cyclopentenones, such as dihydrojasmone and derivatives thereof, preferably the products of formulas IV', IV''' or IVi, preferably in a reaction of the Stetter type.

Advantageously, the mixture of thiamine or a thiamine salt and ascorbic acid in a form which is free or a salt is a mixture comprising an excess of ascorbic acid. The ratio of thiamine/ascorbic in a form which is free or a salt ranges from ½ to 1/20, advantageously from ½ to 1/10, more advantageously from ⅓ to 1/7, and is preferably ⅕ or ⅙.

EXAMPLES

Example 1—Preparation of Diketones

Working Method:

10 mL of anhydrous ethanol, 33.7 mg (0.1 mmol) of thiamine hydrochloride and 119 mg (0.6 mmol) of sodium ascorbate were introduced into a flask equipped with a magnetic stirrer, a condenser and a nitrogen inlet. The mixture was stirred at room temperature for 10 minutes and then 140 mg (2.0 mmol) of 3-buten-2-one and 114 mg (1.0 mmol) heptanal were added. The mixture was stirred at reflux under a stream of dinitrogen during 24 h. The reaction medium became orange at the end of the reaction. This was removed for GC-MS analysis. The diketone produced was purified by evaporating the solvent followed by separation on a silica column (cyclohexane/AcOEt 8/2). The yield was 92%.

The examples presented below were performed:

| $R^1\text{-CHO}$ | $R_3,R_4,\text{A alkene}$ | Product | % yield of final product |
|---|---|---|---|
| 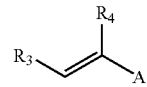 | 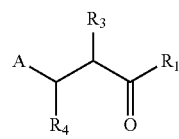 | 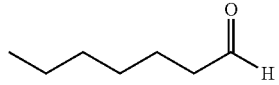 | 92 |
| HCHO | 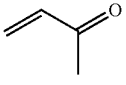 | 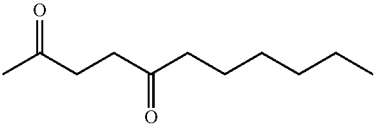 | 35 |
| 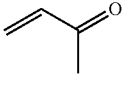 | 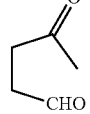 | 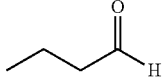 | 74 |
| 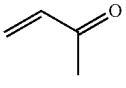 | 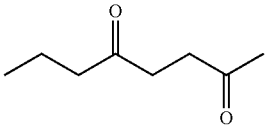 | 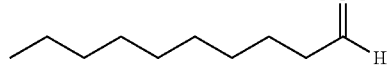 | 66 |
| 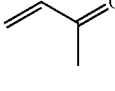 | 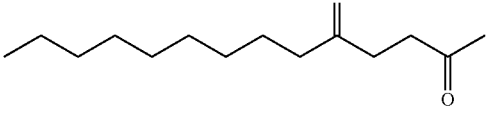 | 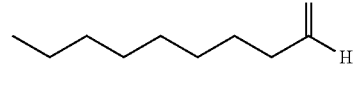 | 69 |
|  | 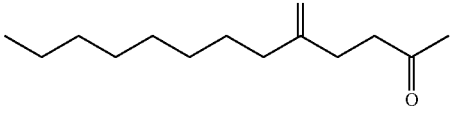 | 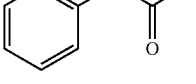 | 74 |
| 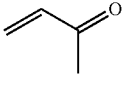 | 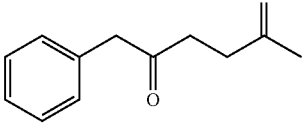 | 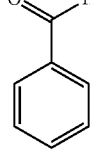 | 27 |
| 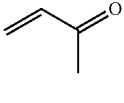 | 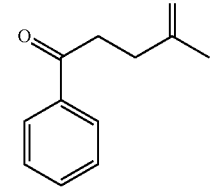 | 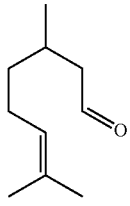 | 39 |

|  | 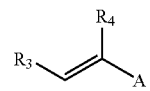 | 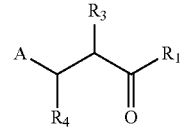 | % yield of final product |
|---|---|---|---|
| 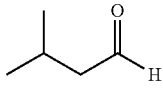 | 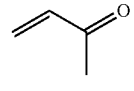 | 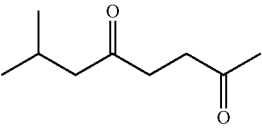 | 73 |
| 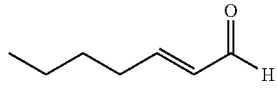 | 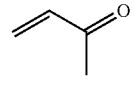 | 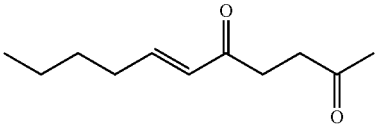 | 49 |
| 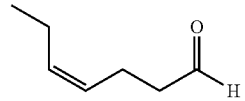 | 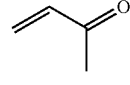 | 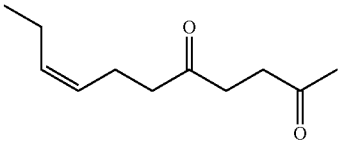 | 64 |
| 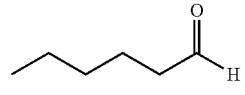 | 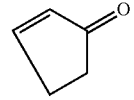 | 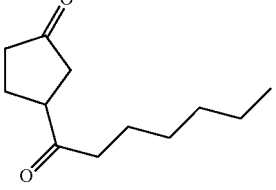 | 31 |

Example 2—Study of Reaction Conditions

The working conditions of the reaction were studied using, as substrate, heptanal and 3-butene-2-one in the following proportions:

|  | m, g | Mr, g/mol | V, mL | n, mol | eq | d, g/mol |
|---|---|---|---|---|---|---|
| heptanal | 0.046 | 114.18 | 0.056 | 0.00040 | 1.00 | 0.82 |
| 3-buten-2-one | 0.056 | 70.09 | 0.065 | 0.00080 | 2.00 | 0.86 |
| sodium ascorbate | 0.048 | 198.12 | — | 0.00024 | 0.60 | — |
| thiamine | 0.013 | 337.23 | — | 0.00004 | 0.10 | — |
| 1,2-PrOH/iPrOH | — | — | 0.100 | — | — | — |

1. Effect of Temperature

The reaction was studied at three different temperatures:

|  | Yield | Conv |
|---|---|---|
| 70° C. | 94% | 68% |
| 80° C. | 92% | 85% |
| 90° C. | 87% | 92% |

The results made it possible to show that the conversion increases with temperature. The yield is best at a temperature of 80° C.

2. Method of Addition

The addition method for vitamins was also studied:

| Duration | T° C. | Conditions of introduction | % dione | % conversion |
|---|---|---|---|---|
| 2 h | 80° C. | Progressive addition of vitamins without solvent (30 min/30 min) | 92 | 85 |
| 2 h | 90° C. | Progressive addition of vitamins without solvent (30 min/30 min) | 87 | 92 |
| 2 h | 80° C. | Progressive addition of vitamins in aqueous solution (30 min/30 min) | 71 | 51 |
| 2 h | 80° C. | Progressive addition of vitamins in iPrOH/H2O (1/1) (30 min/30 min) | 79 | 85 |
| 2 h | 80° C. | Progressive addition of vitamins in iPrOH/H2O (4/1) (30 min/30 min) | 77 | 82 |
| 2 h | 80° C. | Progressive addition of vitamin B1 in iPrOH/1,3-PrOH (1/1) (30 min/30 min) | 87 | 85 |
| 2 h | 80° C. | Progressive addition of vitamin B1 in iPrOH/1,3-PrOH (1/1) (15 min/15 min) | 90 | 84 |
| 2 h | 80° C. | Progressive addition of vitamin B1 in iPrOH/1,3-PrOH (1/1) (8 times with an interval of 15 min) | 94 | 76 |

It was found that the progressive addition of vitamins without solvent or in an alcohol led to a greater conversion and yield.

3. Study of the Amount of Solvent

The reaction between heptanal and 3-buten-2-one was studied in different amounts of solvent (2-propanol):

| | Yield | Conv | |
|---|---|---|---|
| 0.1 mL for 0.05 mL of heptanal | 90% | 84% | 2 × 0.05 eq, 80° C. |
| 0.05 mL for 0.05 mL of heptanal | 75% | 86% | 2 × 0.05 eq, 80° C. |
| 0.05 mL for 0.05 mL of heptanal | 84% | 90% | One pot, 80° C. |
| 0.025 mL for 0.05 mL of heptanal | 83% | 83% | One pot, 80° C. |
| 0.05 mL for 0.05 mL of heptanal | 72% | 92% | One pot, 70° C. |
| 0.05 mL for 0.05 mL of heptanal | 92% | 77% | One pot, 90° C. |

4. Amount of Butenone

The influence of the proportion of 3-buten-2-one was assessed.

| | Yield | Conv |
|---|---|---|
| 2 eq | 84% | 90% |
| 4 eq | 72% | 87% |

The results show that the use of four equivalents of 3-buten-2-one in relation to the heptanal led to a lower yield of 1,4-diketone compared to the use of 2 equivalents.

Example 3—Acyloin Condensation of Heptanol with Vitamins

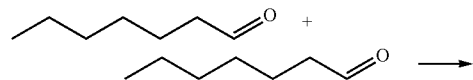

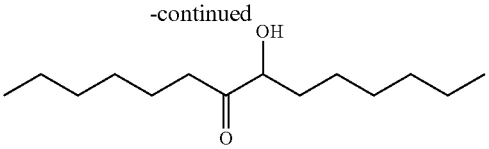

Working Method:

Heptanal (0.1 mL, 0.72 mmol), 3-buten-2-one (0.03 mL, 0.36 mmol), sodium ascorbate (0.086 g, 0.43 mmol), and thiamine (0.024 g, 0.07 mmol) were added to the mixture of iPrOH/1,2-propanediol (1/1) (0.09 mL) at ambient temperature. The reaction mixture was then stirred for 3 hours at 80° C. under inert atmosphere. At the end of 3 hours the reaction crude was analysed by GC/GMS, the desired product having been obtained with a yield of 63% with 57% conversion (in total 36% of product in the reaction crude).

Example 4—Preparation of Cyclopentenones from 1,4-Diketones

Working Method:

10 mL of anhydrous ethanol, 33.7 mg (0.1 mmol) of thiamine hydrochloride and 119 mg (0.6 mmol) of sodium ascorbate were introduced into a flask equipped with a magnetic stirrer, a condenser and a nitrogen inlet. The mixture was stirred at room temperature for 10 minutes and then 140 mg (2.0 mmol) of 3-buten-2-one and 112 mg (1.0 mmol) of hepten-2-al were added. The mixture was stirred at reflux under a stream of dinitrogen during 24 h. The development of the reaction medium was monitored by GC-MS analysis. The cyclopentenone obtained was purified by evaporation of the solvent followed by separation on a silica column (toluene/AcOEt 9/1). The yield was 51%.

Using the working method described above, the following products were obtained:

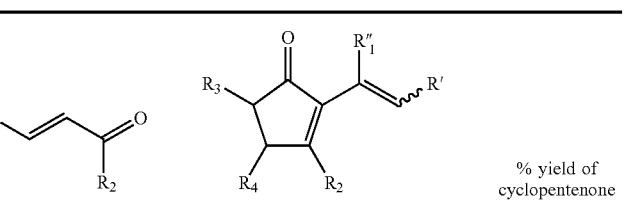

% yield of cyclopentenone

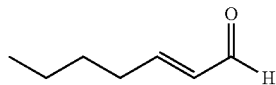 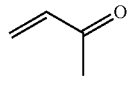 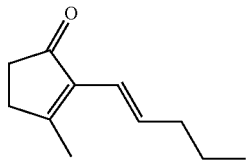

51

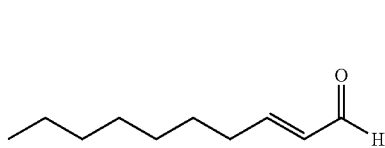 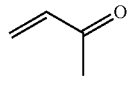 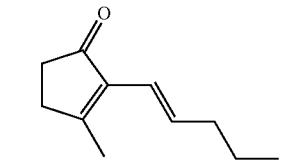

49

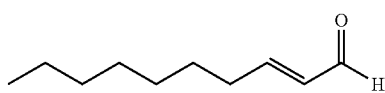 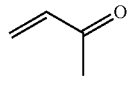 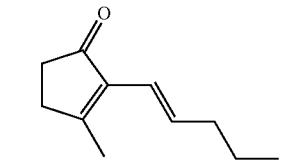

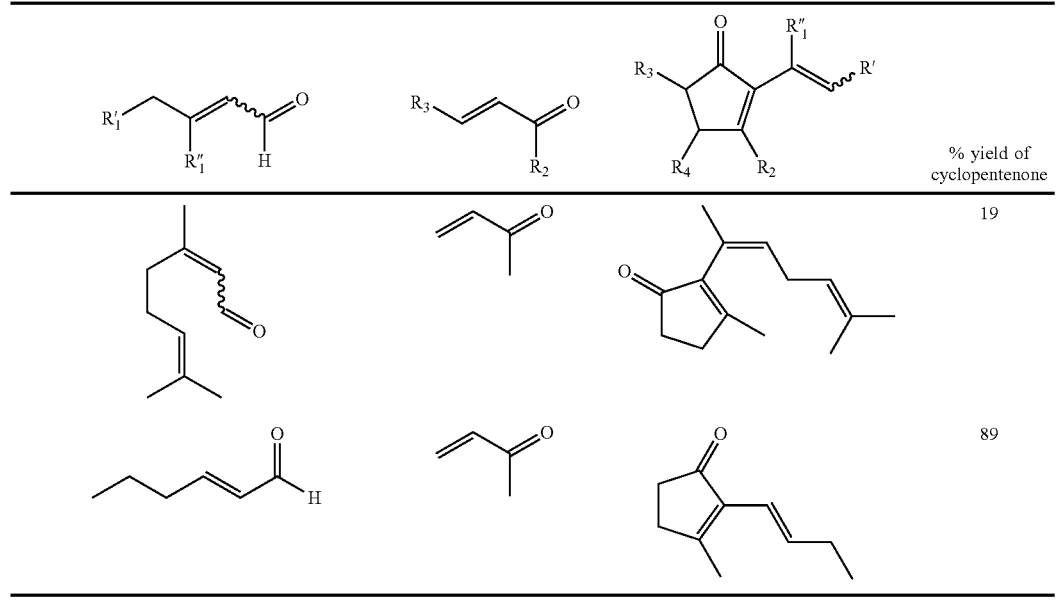

The invention claimed is:

1. A process for preparing a product of formula I:

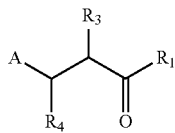

I in which A represents a group selected from:
CO—R$_2$
CO—O—R$_2$a
CN
C(O)—N Ra R'a
CH—(CO$_2$Rb)$_2$ R$_1$ represents a hydrogen atom or a linear or branched alkyl or alkylene group having at most 12 carbon atoms, or R$_1$ represents a saturated or unsaturated cycloalkyl group having from 3 to 7 carbon atoms and optionally comprising one or more heteroatoms selected from the atoms of nitrogen, sulphur or oxygen, or R$_1$ represents a carbocyclic or heterocyclic aryl group, each of these alkyl, alkylene, aryl or cycloalkyl groups being optionally substituted, R$_2$ represents a linear or branched alkyl group having from 1 to carbon atoms, optionally substituted, or R$_2$ represents a saturated or unsaturated cycloalkyl group having from 3 to 7 carbon atoms and optionally comprising one or more heteroatoms selected from the atoms of nitrogen, sulphur or oxygen, or R$_2$ represents a carbocyclic or heterocyclic aryl group, each of these alkyl, aryl or cycloalkyl groups being optionally substituted, R$_2$a represents a linear or branched alkyl group having from 1 to 12 carbon atoms, Ra and R'a, identical or different, are selected from linear or branched alkyl or alkoxy groups having from 1 to 12 carbon atoms, it being understood that Ra and R'a cannot simultaneously represent each a linear or branched alkoxy group having from 1 to 12 carbon atoms, Rb is selected from linear or branched alkyl groups having from 1 to 12 carbon atoms, R$_3$ represents a hydrogen atom, or a linear or branched alkyl or alkylene group having at most 6 carbon atoms, or R$_3$ represents a carbocyclic or heterocyclic aryl group, each of these alkyl, alkylene or aryl groups being optionally substituted, or the groups R$_2$ and R$_3$ are linked together to form a ring having from 5 to 7 carbon atoms, said chain optionally comprising one or more heteroatoms selected from the atoms of nitrogen, sulphur or oxygen, R$_4$ is a hydrogen atom or is selected from optionally substituted alkyl groups, acylamido groups having from 2 to 12 carbon atoms, or carboxyl esters, wherein a product of formula II:

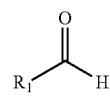

II is reacted with a product of formula III

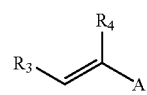

III in the presence of both an organic compound comprising at least one ring selected from a 1,3-imidazolium, a 1,2,4-triazolium or a thiazolium and ascorbic acid in a form which is free or a salt, or a compound comprising a structure

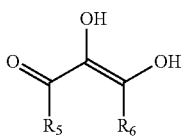

in which $R_5$ and $R_6$ independently of one another represent a hydrogen atom, a linear or branched alkyl group having from 1 to 12 carbon atoms, or $R_5$ and $R_6$ are linked together to form a ring having from 3 to 7 members, said alkyl or said ring being optionally substituted by one or more heteroatoms, especially selected from O, N and S, in an organic solvent.

2. The process according to claim 1, carried out with a product of formula III in which A is C—OR$_2$.

3. The process according to claim 1, in which the reaction is carried out in the presence of both an organic compound comprising at least one thiazolium ring and ascorbic acid in a form which is free or a salt, or a compound comprising a structure

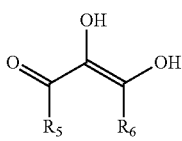

as defined in claim 1, in an organic solvent.

4. The process according to claim 3, in which the reaction is carried out in the presence of both thiamine or a thiamine salt and ascorbic acid in a form which is free or a salt, or a compound comprising a structure

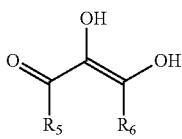

as defined in claim 1, in an organic solvent.

5. The process according to claim 1, wherein the one or more substituents which can be carried by the linear or branched alkyl or alkylene groups, the carbocyclic or heterocyclic aryl groups, or the cycloalkyl groups are selected from the carbocyclic or heterocyclic aryl groups, themselves optionally substituted, the free esterified or a salt carboxylic groups, the free oxo group in the form of a ketone or protected in the form of a ketal, the halogen atoms, and the alkoxy groups having from 1 to 6 carbon atoms.

6. The process according to claim 1 for preparing a product of formula Ia

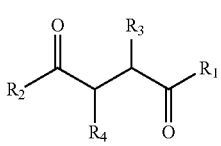

in which $R_1$, $R_3$ and $R_4$ have the meaning as indicated in claim 1 and corresponding to a product of formula I as defined in claim 1, in which A represents a CO—R$_2$ group in which R$_2$ has the meaning as indicated in claim 1, wherein a product of formula II as defined in claim 1 is reacted with a product of formula IIIa:

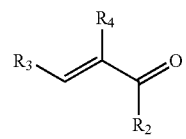

and ascorbic acid in a form which is free or a salt, in an organic solvent.

7. The process according to claim 3, wherein the substituent $R_1$ is selected from a hydrogen atom or a linear or branched alkyl group having from 1 to 9 carbon atoms or a linear or branched alkylene group having at most 9 carbon atoms, a benzyl group or a phenyl group, $R_2$ represents a methyl group, and $R_3$ represents a hydrogen atom.

8. A process for preparing a compound of formula III′:

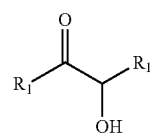

wherein a product of formula II:

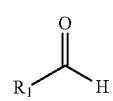

in which:

$R_1$ represents a linear or branched alkyl or alkylene group having at most 12 carbon atoms, or $R_1$ represents a saturated or unsaturated cycloalkyl group having from 3 to 7 carbon atoms and optionally comprising one or more heteroatoms selected from the atoms of nitrogen, sulphur or oxygen, or $R_1$ represents a carbocyclic or heterocyclic aryl group, each of these alkyl, alkylene, aryl or cycloalkyl groups being optionally substituted, is reacted in the presence of both a thiazolium salt, a 1,3-imidazolium salt or a 1,2,4-triazolium salt, as defined in claim 1, and ascorbic acid in a form which is free or a salt, or a compound comprising a structure

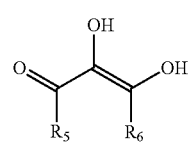

as defined in claim 1, in an organic solvent.

9. The process according to claim 8, in the presence of vitamin B1 and ascorbic acid in a form which is free or a salt.

10. A process for preparing a product of formula IVi

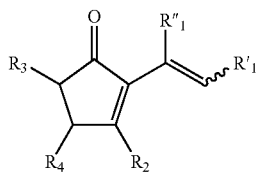

in which $R_2$, $R_3$ and $R_4$ have the meaning indicated in claim 1, in which $R'_1$ represents a linear or branched alkyl or alkylene group having at most 12 carbon atoms, optionally substituted by a carbocyclic or heterocyclic aryl group, a —CHO group, a free esterified or carboxylic salt group, an oxo group, or $R'_1$ represents a carbocyclic or heterocyclic aryl group, and $R''_1$ represents a hydrogen atom or alkyl group having more than 6 carbon atoms, wherein a product of formula IIi

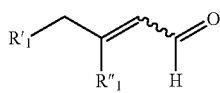

is reacted with a product of formula IIIa:

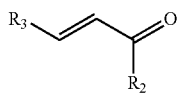

as defined in claim 1 in the presence of thiamine or a thiamine salt, and ascorbic acid in a form which is free or a salt, preferably sodium ascorbate, in an organic solvent to obtain a product of formula Ii:

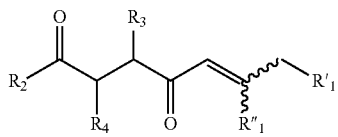

which is a product of formula Ii which is converted spontaneously into a product of formula IVi in the presence of thiamine or a thiamine salt, and ascorbic acid in a form which is free or a salt.

11. A method for the preparation of linear 1,4-dicarbonyl compounds, comprising providing a mixture comprising both an organic component comprising at least one ring selected from a 1,3-imidazolium, a 1,2,4-triazolium or a thiazolium, and ascorbic acid in a form which is free or a salt, and using said mixture to prepare said compound.

12. The method of claim 11 of a mixture comprising both an organic compound comprising at least one thiazolium ring and ascorbic acid in a form which is free or a salt.

13. The method of claim 12 in which the thiazolium is vitamin B1 or a thiamine salt.

14. The method of claim 11, in which the ascorbic acid in a form which is free or a salt is in excess in relation to the thiamine or thiamine salt is in a ratio of from 2/1 to 20/1.

15. The process according to claim 2, in which the reaction is carried out in the presence of both an organic compound comprising at least one thiazolium ring and ascorbic acid in a form which is free or a salt, or a compound comprising a structure

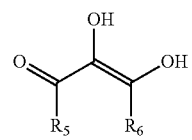

as defined in claim 1, in an organic solvent.

16. The process according to claim 2, wherein the one or more substituents which can be carried by the linear or branched alkyl or alkylene groups, the carbocyclic or heterocyclic aryl groups, or the cycloalkyl groups are selected from the carbocyclic or heterocyclic aryl groups, themselves optionally substituted, the free esterified or a salt carboxylic groups, the free oxo group in the form of a ketone or protected in the form of a ketal, the halogen atoms, and the alkoxy groups having from 1 to 6 carbon atoms.

17. The process according to claim 3, wherein the one or more substituents which can be carried by the linear or branched alkyl or alkylene groups, the carbocyclic or heterocyclic aryl groups, or the cycloalkyl groups are selected from the carbocyclic or heterocyclic aryl groups, themselves optionally substituted, the free esterified or a salt carboxylic groups, the free oxo group in the form of a ketone or protected in the form of a ketal, the halogen atoms, and the alkoxy groups having from 1 to 6 carbon atoms.

18. The process according to claim 1, wherein $R_4$ represent a hydrogen atom.

19. The process according to claim 1, wherein the compound comprising a structure

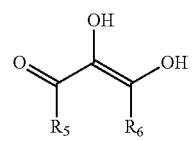

is a reductone.

20. The process according to claim 19, wherein the compound the compound comprising a structure

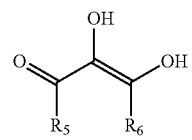

is 2-hydroxypropanedial or 2,3-dihydroxycyclopent-2-en-1-one, or croconic acid.

21. The process according to claim 14, wherein the ratio is from 2/1 to 10/1.

* * * * *